US006619286B2

(12) United States Patent
Patel

(10) Patent No.: US 6,619,286 B2
(45) Date of Patent: Sep. 16, 2003

(54) PRESSURE REGULATOR FOR A RESPIRATOR SYSTEM

(75) Inventor: Kaushik I. Patel, Greenford (GB)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/881,415

(22) Filed: Jun. 14, 2001

(65) Prior Publication Data

US 2002/0073994 A1 Jun. 20, 2002

(30) Foreign Application Priority Data

Jun. 16, 2000 (GB) ............................................ 0014713

(51) Int. Cl.[7] ......................... A61M 16/00; A62B 7/04; F16K 31/26

(52) U.S. Cl. ........................... 128/204.26; 128/201.24; 128/201.28; 128/204.18; 128/205.11; 128/205.24; 128/205.25; 251/118; 251/127

(58) Field of Search ...................... 128/201.24, 201.28, 128/204.18, 205.11, 205.12, 205.23, 205.24, 205.25, 206.15, 206.23, 206.24, 200.27, 200.28, 201.22, 201.23, 201.29, 204.26; 251/127, 118

(56) References Cited

U.S. PATENT DOCUMENTS 3,752,175 A * 8/1973 Hamilton et al. .......... 137/81.1
4,083,380 A 4/1978 Huber
4,352,373 A * 10/1982 Kay et al. ............... 137/561 A
4,397,331 A * 8/1983 Medlar ....................... 137/375
4,398,563 A * 8/1983 Kay et al. ...................... 138/42
4,429,714 A * 2/1984 Hughes et al. ........... 137/625.3
4,449,524 A 5/1984 Gray
4,693,450 A * 9/1987 Paetzel ....................... 251/121
4,739,795 A 4/1988 Ewbank et al.
4,899,740 A * 2/1990 Napolitano ............ 128/202.22
5,018,703 A * 5/1991 Goode ........................ 251/127
5,161,576 A * 11/1992 Hekkert et al. ........ 137/614.18
5,265,592 A * 11/1993 Beaussant .............. 128/201.24
5,855,355 A * 1/1999 Grunert et al. ............. 251/120
5,890,505 A * 4/1999 Boger ............................ 137/1
5,924,673 A * 7/1999 Welker ....................... 251/118
6,038,742 A * 3/2000 Patterson .................... 24/3.12
6,105,928 A * 8/2000 Ise et al. .................. 251/61.2
6,206,257 B1 * 3/2001 Peele et al. ................. 224/197
6,289,934 B1 * 9/2001 Welker ......................... 138/39
6,302,105 B1 * 10/2001 Wickham et al. ...... 128/204.18
6,394,088 B1 * 5/2002 Frye et al. ............ 128/204.26
6,394,091 B1 * 5/2002 Giorgini ................ 128/206.21
6,427,690 B1 * 8/2002 McCombs et al. ..... 128/204.26
6,439,267 B2 * 8/2002 Welker ........................ 138/39

FOREIGN PATENT DOCUMENTS

DE 1129376 5/1962
DE 3637409 5/1988
WO WO 97/44093 11/1997

* cited by examiner

*Primary Examiner*—Weilun Lo
*Assistant Examiner*—Michael G. Mendoza
(74) *Attorney, Agent, or Firm*—Karl G Hanson

(57) ABSTRACT

A regulator assembly is provided for use in a respirator system to supply a regulated flow of air to a respirator head piece. The respirator assembly comprises a housing (15) having an air inlet port (17) for connection to a source of air at comparatively high pressure, and an air outlet port (23) for connection to the respirator head piece. The housing (15) contains an air pressure-reduction stage (19) in communication with the inlet port (17), and a noise-reduction stage (21) between the pressure-reduction stage and the outlet port (23). The noise reduction stage (21) comprises two, spaced, muffler discs (41, 43) the first of which is positioned adjacent the air outlet (39) of the pressure-reduction stage (19). A deflector plate (47) deflects the airflow from the pressure-reduction stage (19) through the first muffler disc (41), and thereby diffuses the air flow before it reaches the second muffler disc (43).

9 Claims, 8 Drawing Sheets

PRESSURE REGULATOR FOR A RESPIRATOR SYSTEM

This application claims priority from Great Britain Application No. GB 0014713.2 filed Jun. 16, 2000.

The present invention relates to respirator systems of the type that provide a forced flow of air to the respirator wearer from a source of compressed air.

BACKGROUND

One common purpose of a respirator is to prevent contaminants from entering the respiratory system of the wearer. A respirator typically comprises a head piece in some form, shaped to provide a breathing zone around at least the nose and mouth of the wearer. In some respirators, the breathing action of the wearer alone causes air to be drawn into the breathing zone through a filter. Other respirators, however, provide a forced flow of filtered air to the breathing zone, thereby relieving the wearer of the need to inhale against the resistance of the filter and, at the same time, ensuring that any leakage in the respirator is outwards (that is, away from the breathing zone rather than into it). Respirators that use forced air flow are preferred in certain working environments, particularly those that are physically demanding on the wearer and those where the wearer is likely to benefit from the cooling effect of air flowing through the breathing zone.

A forced flow of air into the breathing zone of a respirator head piece may be generated by a fan or by a blower which, together with its power source, may be carried by the respirator wearer (known as a powered system). Alternatively, the forced flow of air may be obtained from a source of compressed air, which may be either fixed or portable (known as a supplied air system). In that case, the respirator head piece is connected to the air source through a regulator, to reduce the pressure at which air is supplied to the head piece to a suitable level. Examples of respirator head pieces suitable for use in supplied air systems are described in EP-A-0 602 847; GB-A-2 032 284, and in U.S. Pat. Nos. 3,963,021 and 4,280,491. In some supplied air systems, the pressure regulator is part of the equipment that is carried by the respirator wearer, in which case it is typically mounted on a belt at the wearer's waist and is provided with a control knob, accessible to the wearer, by which the flow of air into the head piece can be adjusted. In other systems, in which the compressed air is provided through a wall-mounted socket, the pressure regulator may be located at the socket.

A so-called "self-contained breathing apparatus", intended for use in a toxic environment or under water, also supplies the user with air obtained from a source of compressed air via one or more pressure regulators. In that case, however, the head piece is in the form of a tightly-fitting mask as described, for example, in WO 97/30753 and 97/46281, and in EP-A-0 631 795, 0 766 979 and 0 921 066. Generally, the compressed air pressures used in this type of system are comparatively high and the pressure regulator arrangements that are used are consequently more complex than those used in supplied air systems, for which standard (lower cost) regulator devices have typically been employed despite the fact that they offer the user much less control over the air flow into the head piece.

Sources of compressed air generate noise and, in the case of respirator systems and breathing apparatus, that noise can be transmitted to the head piece or mask and thus to the ears of the user. Despite the fact that exposure to such noise can be extremely unpleasant, noise reduction in respirator systems does not receive much attention and is often ignored completely. Examples of respirator systems that do incorporate noise reduction arrangements are those available, under the trade designations "Airstream AH 18" and "Visionair", from Minnesota Mining and Manufacturing Company of St. Paul, Minn., USA. In the first-mentioned system, noise reduction is provided by two sintered discs contained in the low-pressure hose leading from the pressure regulator to the respirator head piece and, in the second system, it is provided by muffling the air supply tube within the head piece itself.

The cost of a respirator system is a particularly important factor because, even if a system offers particular advantages, users may be tempted for costs reasons to make do with an inferior system. Thus, although effective pressure regulation and noise reduction are known to be beneficial to the wearer and would make the use of a supplied air respirator system less unpleasant, they are often not provided for reasons of cost. The present invention is concerned with enabling pressure regulation and noise reduction to be provided in a respirator system at an acceptable cost.

SUMMARY OF THE INVENTION

The present invention provides a regulator assembly for use in a respirator system to supply a regulated flow of air to a respirator head piece; the assembly comprising:

a housing that comprises an air inlet port for connection to a source of air at comparatively high pressure, and an air outlet port for connection to the respirator head piece; the housing containing an air pressure-reduction stage in communication with the inlet port, and a noise-reduction stage located in the air flow path within the housing between the pressure-reduction stage and the outlet port; wherein the noise-reduction stage comprises first and second noise-reduction members spaced apart from each other along the air flow path, the first noise-reduction member being positioned adjacent the air outlet of the pressure-reduction stage, and including a deflector member arranged to deflect the air flow from the pressure-reduction stage through the first noise-reduction member and thereby diffuse the air flow before it reaches the second noise-reduction member.

As used herein, the term "air" includes breathable gases.

Through an appropriate configuration of the pressure-reduction stage that forms part of an assembly in accordance with the invention, a standard assembly that is suitable for use in many different supplied air respirator systems can be readily provided. This standardization offers the possibility of substantial cost reduction, making it possible in turn to provide effective pressure regulation and noise reduction in supplied air respirator systems at a reasonable price.

BRIEF DESCRIPTION OF THE DRAWINGS

By way of example only, a regulator assembly in accordance with the invention will be described with reference to the accompanying drawings, in which.

DETAILED DESCRIPTION OF THE PREFERRED EMBODIMENTS

Figure 1:
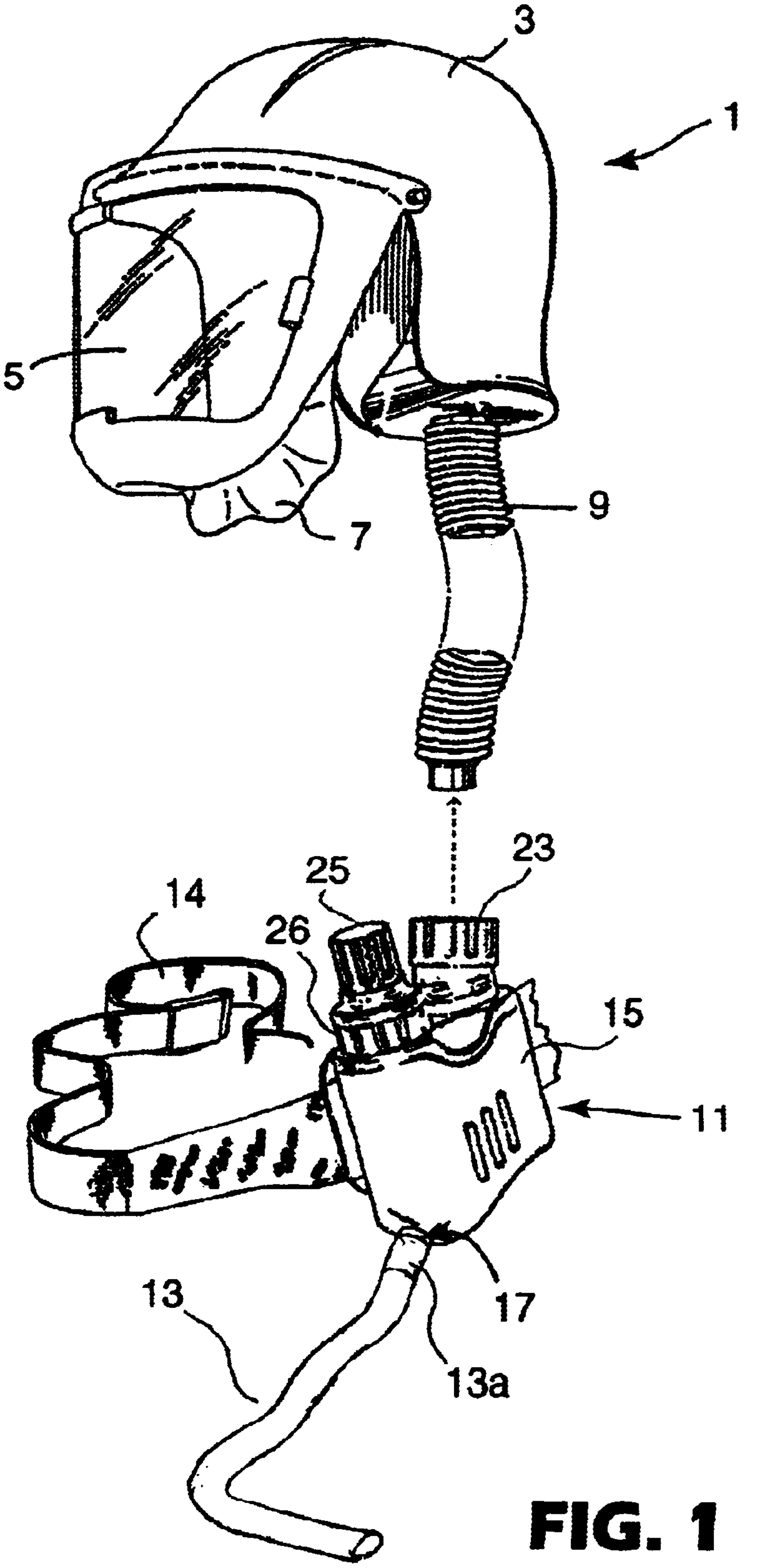
FIG. 1 is a perspective view of a respirator system that incorporates a regulator assembly in accordance with the invention.

The respirator shown in FIG. 1 includes headgear in the form of a helmet 1 which, in use, defines a substantially closed breathing zone around part of the wearer's head including the wearer's nose and mouth. The helmet 1 comprises (i) a shell 3 that is intended to extend over the top, back and sides of the head of the respirator wearer, and (ii) a visor 5 that extends downwards from the front of the shell to cover the face of the wearer. In use, the shell 3 is supported on the wearer's head by a harness (not visible in the drawing), and a seal (also not visible in the drawing) is provided to close the gap between the shell 3 and the wearer's head while a flexible membrane 7 extends from the lower edge of the visor 5 to bear against the wearer's chin and close the bottom of the helmet.

A flexible, low-pressure hose 9 extends from the rear of the helmet 1 to connect the interior of the helmet, via a regulator assembly 11 and a flexible, high-pressure air line 13, to a source of filtered compressed air (not shown). The filtered compressed air may be provided through a fixed wall-mounted socket (not shown), to which the remote end of the high-pressure line 13 is releasably connected, possibly via an additional filtration unit to remove particulates, moisture and/or odour. Alternatively, the source of compressed air may be a compressed air cylinder with a suitable pressure regulator.

The regulator assembly 11, which is described in greater detail below, is provided with a belt 14 so that it can be worn at the wearer's waist.

When the respirator is in use, filtered air from a compressed air source is supplied, through the high-pressure line 13, to the regulator assembly 11 in which the pressure of the air is reduced in order to provide a flow of air that meets the safety requirements to which the respirator is directed, and also the requirements of the respirator wearer. The air is then delivered by the low-pressure hose 9 into the breathing zone (defined by the helmet 1 around the wearer's head), and is inhaled by the wearer. Surplus filtered air and exhaled air leave the breathing zone through natural leakage at the seals or through vents that are formed in the helmet 1 adjacent the wearer's mouth specifically for that purpose. In some cases, a one-way outlet valve is provided in the helmet adjacent the wearer's mouth to provide a route by which surplus filtered air and exhaled air can leave the breathing zone, but that is not essential. The rate at which surplus filtered air and exhaled air leave the helmet typically causes a slight positive pressure (of about 2 to 4 Pa) to build up within the breathing zone, but that is also not essential.

The regulator assembly 11 will now be described in greater detail with reference to FIGS. 2 to 5, which show the assembly disconnected from the respirator system. The various components of the assembly 11 are contained within a casing 15 that has an input port 17 at one lower corner through which compressed air enters the assembly. From the input port 17, the air passes through an odour filter 18 to a pressure-reduction stage, indicated generally at 19, and then through a noise-reduction stage 21, before leaving the assembly through an outlet port 23 on the top of the casing. In use, the high-pressure line 13 may be attached to the regulator assembly 11 by a compressed air quick-release coupling 13*a* (FIG. 1) of any suitable type at the input port 17, and the low-pressure hose 9 is attached to the outlet port 23, for example by a bayonet connection. A bracket 24 can be located on the back of the casing 15 through which the belt 14 can be threaded to mount the regulator assembly 11 at the waist of the respirator wearer. Advantageously, the bracket 24 is secured to the casing 15 by a rivet 24*a* that permits pivotal movement of the assembly 11 relative to the bracket when the respirator is in use. The regulator assembly 11 can thus swivel and adjust its orientation in response to movement of the respirator wearer.

The pressure-reduction stage 19 of the assembly comprises a pressure regulator that functions to reduce the pressure of the incoming air from a value typical of the compressed air source (generally in the range of 2 to 10 bar) to a level that will provide an appropriate flow of air into the helmet 1 of the respirator system (FIG. 1). Typically, the pressure of the air leaving the regulator will be in the range of about 1.5 to 2 bar. Pressure regulators are well known devices and exist in many different forms as can be seen, for example, from WO 99/13945 and 97/13185; U.S. Pat. Nos. 5,586,569, 3,926,208 and 3,811,400; and EP-A-0 586 078 and 0 303 583.

Advantageously, the regulator employed for the pressure reduction stage 19 of the assembly 11 is one that, for a given regulator setting, will provide a substantially constant flow of air for any inlet pressure in the range of at least 3 to 8 bar (and preferably in the range of from 2 to 10 bar). Desirably, the regulator should be capable of providing a substantially constant flow of air at a selected level within the range of about 150 1/mm to about 305 1/mm. A control knob 25 on the top of the regulator projects from the casing 15 of the assembly 11 to enable the flow of air from the respirator to be adjusted. The control knob 25 is accessible to the respirator wearer when the respirator is in use, and is provided with a locking collar 26 so that it can be fixed in any desired position.

Figure 6:
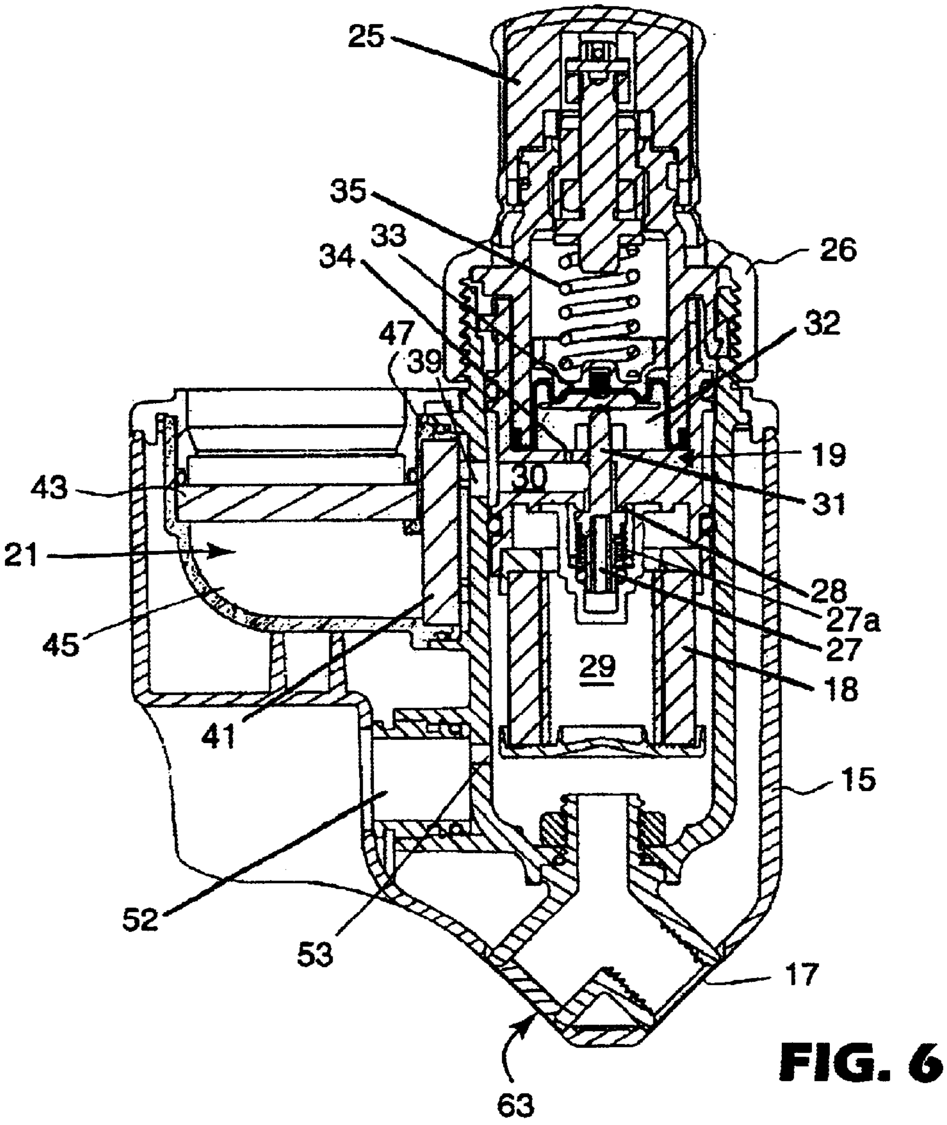
FIG. 6 is similar to FIG. 5 but shows, in greater detail, the components of a regulator that forms part of the assembly.

The construction and operation of a preferred form of regulator will now be described briefly with reference to FIG. 6. It should be noted that some of the components of the regulator have been omitted from FIG. 4 for the sake of clarity.

The regulator comprises a balanced poppet valve 27, 28 controlled by a pressure-responsive diaphragm 33 to provide accurate pressure (and hence flow) regulation. The poppet valve comprises a valve poppet assembly 27 urged by a light spring 27*a* into cooperation with a valve seat 28 to control the flow of air from an input passage 29 on the downstream side of the filter 18 to an output passage 30. From the output passage 30, the air (which is now at a reduced pressure) passes to the outlet port 23 of the regulator assembly 11 through the noise reduction stage 21 which will be described in greater detail below. A stem 31 of the valve poppet 27 extends into a control chamber 32 on one side of the pressure-responsive diaphragm 33, that chamber being in communication, through an aperture 34, with the output passage 30. The diaphragm 33 is biased, from the other side, by a spring 35 the pressure of which is adjusted by turning the control knob 25.

When the control knob 25 is at one end of its range, whereby the pressure applied to the diaphragm 33 by the spring 35 is at a minimum, the regulator functions to deliver a substantially constant minimum flow of air (typically about 150 l/min) to the outlet port 23 of the regulator assembly 11, over the normal range of input pressures from the compressed air source. This is achieved as follows:

The diaphragm 33 adopts a position determined by the spring 35 and, in turn, adjusts the position of the valve poppet assembly 27 relative to the valve seat 28. Air supplied by the high-pressure hose 13 flows through the poppet valve, and the resulting pressure in the output passage 30 is communicated through the aperture 34 to the control chamber 32, causing an adjustment in the position of the diaphragm 33 (and hence in the position of the valve poppet assembly 27 relative to the valve seat 28) until equilibrium is achieved. Any fluctuations in the air supply pressure, or change in the pressure at the outlet port 23 (which could be caused, for example, by a kink in the low-pressure hose 9) is reflected in the pressure in the output passage 30 and immediately results in a re-adjustment of the position of the diaphragm 33 (and hence in the position of the valve poppet assembly 27 relative to the valve seat 28) to maintain the flow of air from the regulator substantially constant at the required minimum level.

The minimum air flow level provided by the regulator assembly is generally selected to provide to the respirator wearer with protection sufficient to satisfy regulatory requirements. If the respirator wearer requires an increased flow of air into the helmet 1 (i.e. greater than the 150 l/min. mentioned above for example, to provide increased cooling), he/she adjusts the control knob 25 to increase the pressure applied by the spring 35 to the diaphragm 33 and thus move the valve poppet assembly 27 further from the valve seat 28. Thereafter, the regulator functions as described above to maintain the output flow substantially constant at the new level despite fluctuations or changes in the air supply pressure, or changes in the pressure at the outlet port 23.

It will be appreciated that the regulator employed as the pressure reduction stage 19 of the assembly 11 need not have the particular construction described above with reference to FIG. 6 and that other forms of regulator could be used. However, the use of a regulator that will respond rapidly to deliver a substantially constant output pressure (and hence a substantially constant flow of air) for any particular setting of the control knob 25 across the normal range of input pressures from the compressed air source is preferred. The regulated flow of air then passes to the outlet port 23 of the assembly 11 via the noise reduction stage 21, shown in both FIGS. 5 and 6.

The noise-reduction stage 21 of the assembly 11 comprises two muffler discs 41, 43 formed of a noise-reduction material and located in the flow path of air from the output passage 30 of the pressure-reduction stage 19. The discs are separated from each other by a chamber 45. The discs 41, 43 may be formed from any suitable material, for example a sintered polymeric or metallic material, and need not both be formed from the same material. Examples of suitable materials for the discs 41, 43 are high density polyethylene and polypropylene having a thickness of about 6 mm. The first muffler disc 41 is located immediately in front of the outlet 39 from the passage 30, with one of its plane surfaces directed towards the outlet so that air emerging from the passage 30 impinges on a region in the upper part of the disc (as seen in FIG. 6). The cross-sectional area of the outlet 39 is typically very small in comparison to the area of the plane face of the disc and, if the air from the outlet 39 were to pass straight through the disc, the muffling effect of the latter would be comparatively small. To prevent that, a deflector plate 47, formed as part of the moulding of the casing 15, is provided to cover the upper half of the disc 41 on the side opposite the outlet 39, thereby diverting air down through the disc so that is emerges prom the lower half of the disc into the chamber 45. The first disc 41 thus muffles the noise of the air emerging from the regulator outlet 39 and, in combination with the deflector 47, also serves to diffuse the air flow. The flow is diffused further in the chamber 45 and turned through 900 before it impinges on, and passes through, the second muffler disc 43 in which further noise reduction occurs. The air then leaves the assembly 11 through the outlet port 23 which, advantageously, is inclined to the vertical as shown in the drawings and rotatable on a seat 49 to accommodate various positions of the low-pressure hose 9.

The use of the deflector plate 47 not only enables the disc 41 to have a muffling effect despite being located immediately adjacent the regulator outlet 39 but actually enhances the effect because it encourages the air to flow through a large area of material. The use of two muffler discs 41, 43 is advantageous because it enables a desired noise reduction to be achieved using a more porous material than would be necessary if only one disc were used. Preferably, the noise-reduction stage 21 of the assembly 11 reduces the noise level as measured at the ear of the wearer to a level of less than 65 dB.

Figure 5:
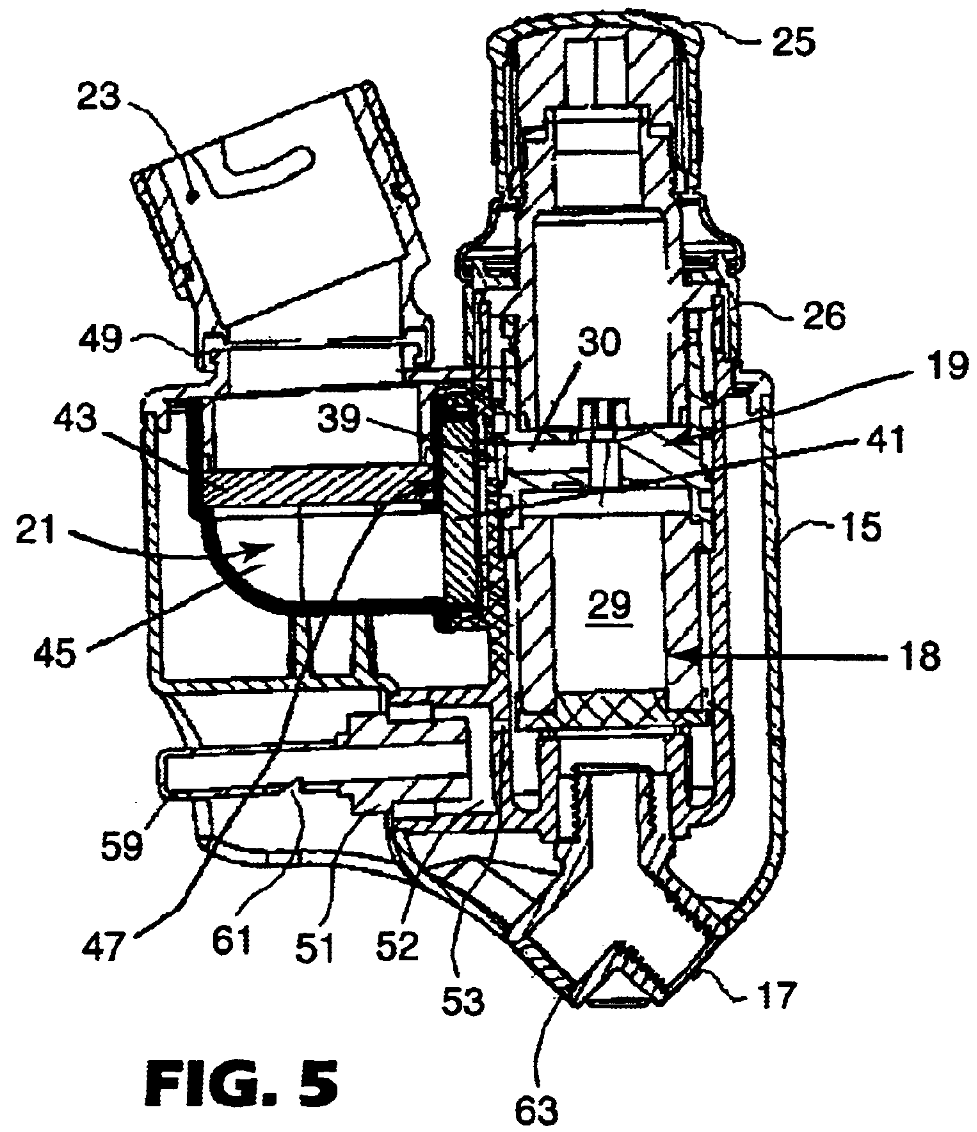
FIG. 5 is a vertical cross-sectional view through the regulator assembly, on the line V—V of FIG. 4, from which some components have been omitted for clarity.
Figure 7:
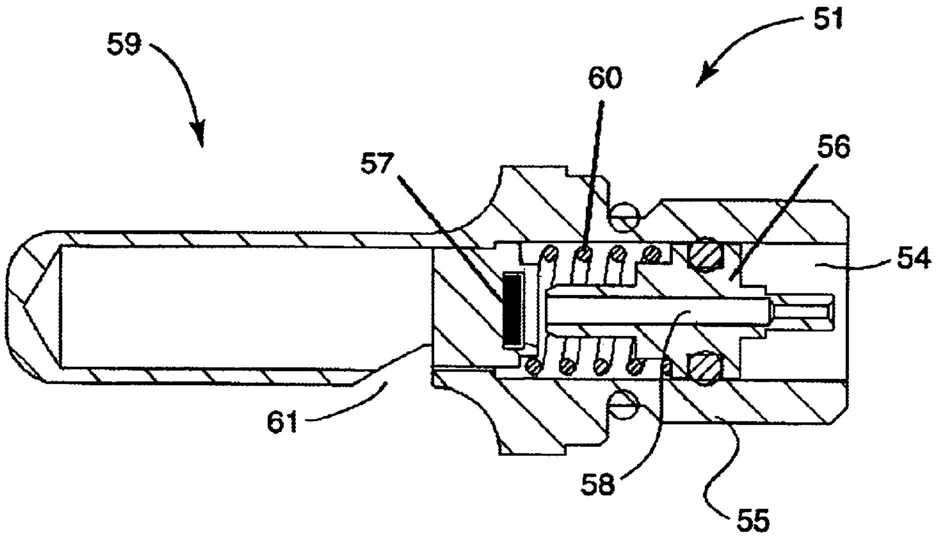
FIG. 7 is a vertical cross-sectional view, on the same line as FIG. 5, through a whistle that forms part of the assembly.

The odour filter 18 in the regulator assembly 11 is provided to reduce odours in the compressed air systems, which would otherwise be carried with the air into the respirator helmet 1. The odour filter is not essential to the operation of the regulator assembly 11 and could be omitted. In FIGS. 5 and 6 the odour filter 18 is located in the input to the pressure-reduction stage 19 of the assembly, but that location is not essential and the filter could be positioned elsewhere in the air flow path on the high pressure side of the regulator 19 (including outside the casing 15). The odour filter 18 can be of any suitable type, for example a carbon filter. The regulator assembly 11 also includes a whistle 51, located in a port 52 the lower part of the casing 15, to provide a warning to the respirator wearer in the event that the pressure of the air supplied via the high pressure hose 13 falls below a certain level. The port 52 is in communication, through an aperture 53, with the input port 17 of the regulator assembly 11 whereby the pressure of the air supplied by the high-pressure hose 13 to the odour filter 18 is applied also to the adjacent, open, end 54 of the main body 55 of the whistle 51 (see also FIG. 7 which shows the whistle in greater detail, removed from the regulator assembly 11). The body 55 of the whistle contains a piston 56 one end face of which is exposed to the pressure at the open end 54. At the other end, the piston 56 co-operates with a valve spat 57 to form a whistle valve controlling the passage of air from the open end 54, via a longitudinal bore 58 within the piston, to the whistle flute 59 which projects from the casing 15 of the regulator assembly 11 and is visible in FIG. 2. A spring 60 acts on the piston 56 to urge the latter away from the valve seat 57 and permit the passage of air through the whistle. During normal operation of the respirator system, however, the pressure of the air supplied to the input port 17 of the regulator assembly 11 (and thus to the end face of the piston 56) is sufficient to overcome the action of the spring 56 and to hold the piston against the valve seat 57 so that the whistle valve is closed. Only in the event of the supplied air pressure falling below a predetermined level (for example, 2.5 bar) will the spring 60 move the piston away from the valve seat, permitting air to flow along the bore 58 and exit the regulator assembly 11 via the aperture 61 of the flute 59, causing the latter to sound and give a warning to the respirator wearer of a potentially dangerous situation. Other forms of warning device could be used instead of the whistle 51, for example, other audible devices such as bells and also sensory warning devices, and that it is not essential for the warning device to form part of the regulator assembly 11 although it is convenient for it to do so.

Figure 2:
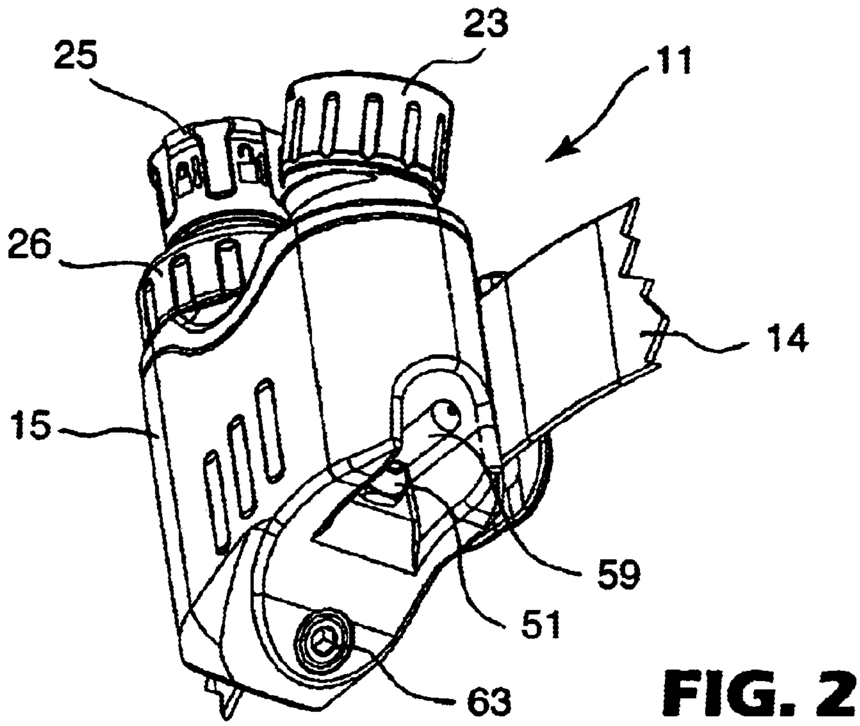
FIG. 2 is an enlarged perspective view, from below and to one side, of the regulator assembly of FIG. 1.
Figure 3:
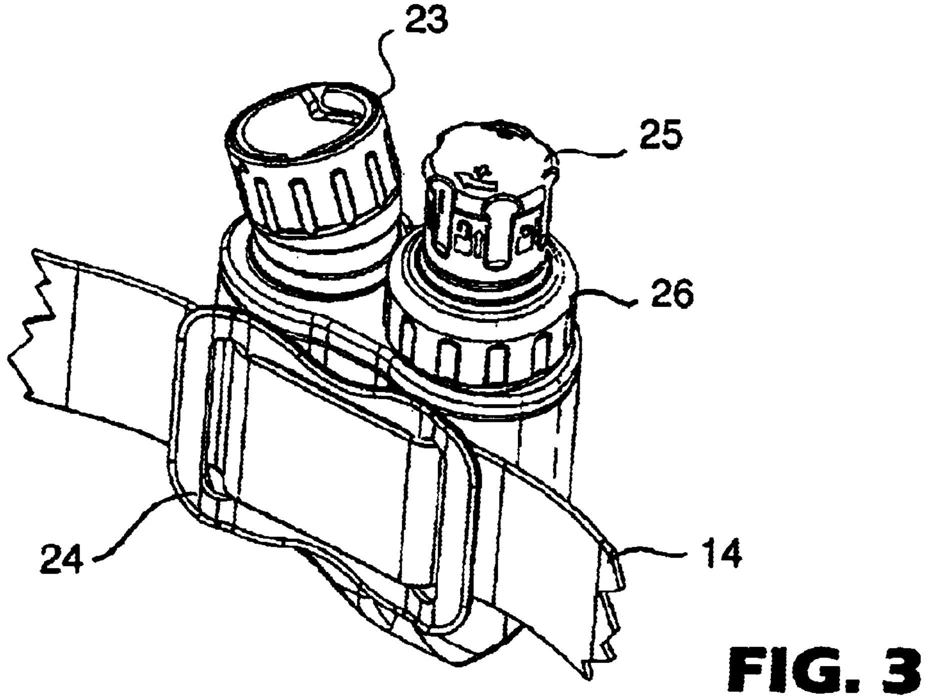
FIG. 3 is a perspective view from the rear of the regulator assembly.
Figure 4:
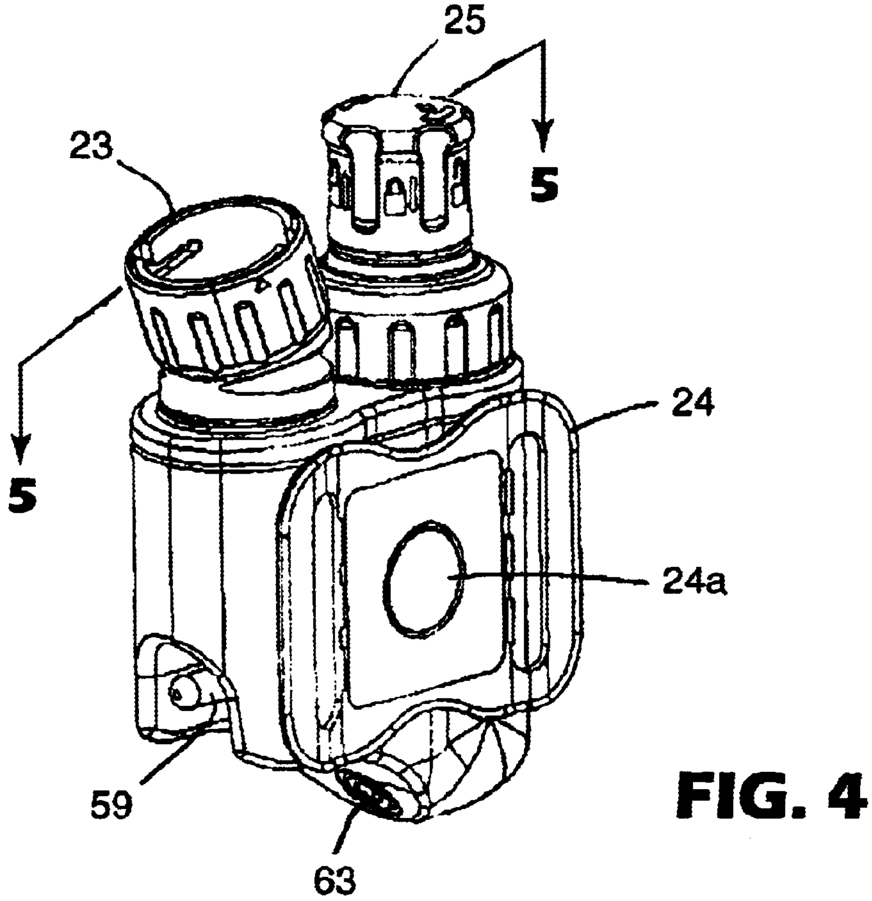
FIG. 4 is another perspective view from the rear of the regulator assembly, from which a belt that carries the assembly has been omitted.

The regulator assembly 11 further includes an outlet 63 adjacent, and in communication with, the high pressure inlet 17 for the connection, if desired, of a spray gun (not shown). This arrangement thus enables the connection of a spray gun to the same high-pressure hose that is used to supply the respirator. If the outlet 63 is not required, it is blanked off as shown in FIGS. 2 and 4. The symmetrical arrangement of the high-pressure inlet 17 and outlet 63 relative to the filter 18, as illustrated in FIGS. 5 and 6, enables these two ports to be interchanged if desired.

A regulator assembly as described above with reference to FIGS. 2 to 7 can be manufactured as a standard unit that will provide, for a variety of supplied air respirator systems, not only the essential function of reducing the pressure of the air before it reaches the respirator head piece but also the highly desirable function of reducing the noise that reaches the ears of the respirator wearer from the compressed air system. The particular regulator assembly 11 described above offers the additional advantageous feature that, for any one setting of the control knob 25, the flow rate of air into the respirator head piece will be substantially constant. The same standard unit can additionally provide an odor filter, an audible warning device, and a connection for a spray gun. The configuration of the various components of the assembly, illustrated in FIGS. 5 and 6, results in a compact unit that does not inconvenience the wearer and which, through a suitable choice of materials, is comparatively light in weight. The sizes of inlet and outlet ports 17, 23, 63 of the assembly are selected for connection to standard hoses but could be provided with adaptors for connection to non-standard hoses if required.

The headpiece 1 of the respirator may take other forms than that shown in FIG. 1. For example, the head piece may retain the helmet form shown in FIG. 1 but be provided, additionally, with a hard hat inside the shell 3, which fits around and further protects the head of the wearer. In another case, the headpiece may be required to provide only respiratory protection for the wearer. In that case, it may comprise simply a face mask or visor (possibly with a hood to cover, but without providing protection for, the head of the wearer).

Figure 8:
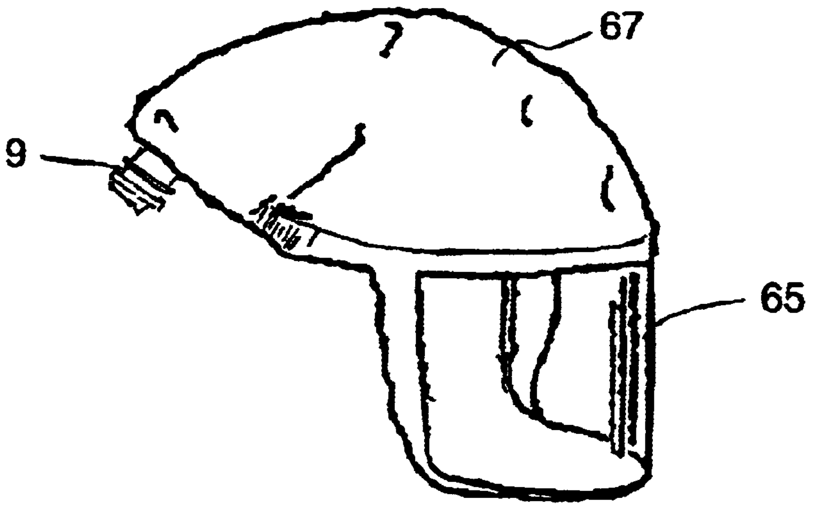
FIGS. 8 to 11 illustrate other respirator head pieces that can be used with the regulator assembly of FIGS. 2 to 6.

FIG. 8, for example, shows a head piece comprising a visor 65 with a loose fitting hood 67 at the rear of which is the low pressure hose 9 providing a passage for a forced air flow from the regulator assembly 11 (not shown) into the head piece.

Figure 9:
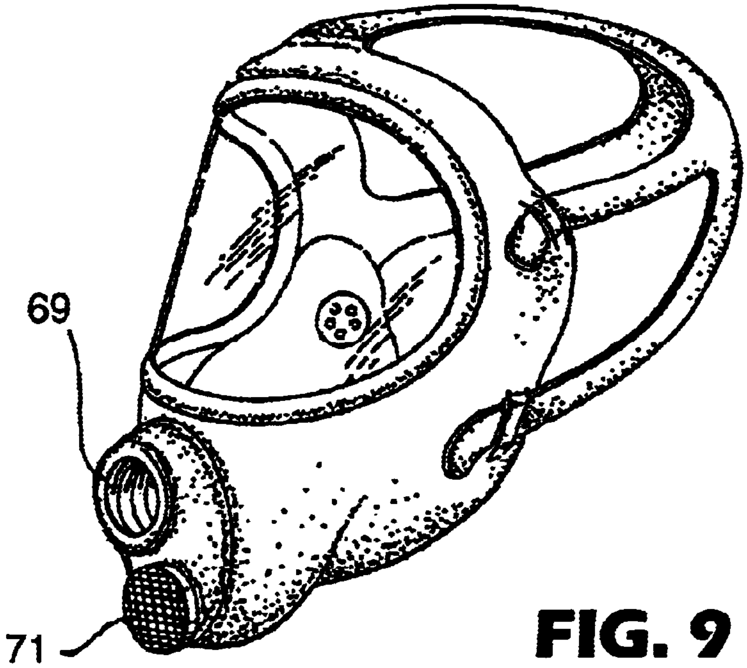

FIG. 9 shows a full face mask intended to cover the eyes as well as the nose and mouth of the wearer, with an air inlet 69 for connection to the low pressure hose 9 (not shown) provided at the front of the mask. In this case, the mask also has an outlet valve 71 positioned adjacent the air inlet 69 to provide a route by which surplus filtered air and exhaled air can leave the mask.

Figure 10:
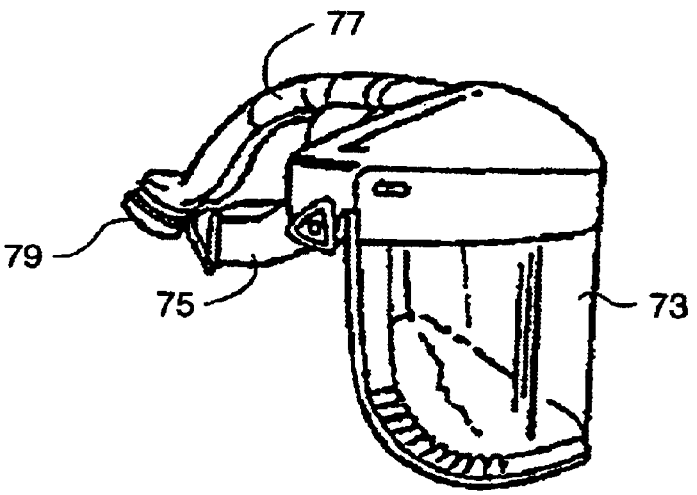

FIG. 10 shows a head piece comprising a visor 73 and a head harness 75, and an air duct 77 extending over the top of the wearer's head to carry a forced flow of air to the inside of the visor. In this case, the low pressure hose 9 (not shown) from the regulator assembly would be connected to the inlet 79 of the air duct 77.

Figure 11:
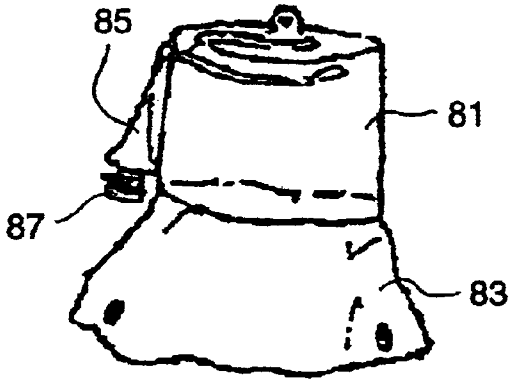

FIG. 11 shows yet another head piece comprising a generally cylindrical head enclosure 81 formed from a transparent material and provided with a cape 83 for covering the upper part of the body of the wearer. The head piece has a supply pipe 85 for carrying a forced flow of air to the interior of the head enclosure 81, the inlet of 87 of the supply pipe being connected, in use, to the low pressure hose 9 (not shown) from the regulator assembly.

Any of the respirator head pieces illustrated in FIGS. 1 and 5 to 8 can, if required, be provided with an indicator device that is capable of warning the wearer in the event that the air flow into the breathing zone within the helmet falls below a safe level. Examples of such indicator devices are described in DE-A-30 32 371, GB-A-2 130 893, U.S. Pat. No. 4,765,326, and in EP-A-0 349 191 and 0 602 847.

What is claimed is:

1. A regulator assembly for use in a respirator system to supply a regulated flow of air to a respirator head piece; the assembly comprising:

a housing that comprises (a) an air inlet port for connection to a source of air at comparatively high pressure, and (b) an air outlet port for connection to the respirator head piece;

the housing having an air flow path between the air inlet port and the air outlet port, the housing containing (1) an air pressure-reduction stage in communication with the inlet port, and (ii) a noise-reduction stage located in the air flow path within the housing between the pressure-reduction stage and the outlet port;

wherein the noise-reduction stage comprises first and second noise-reduction members spaced apart from each other along the air flow path, the first noise-reduction member being positioned adjacent the air outlet of the pressure-reduction stage, and including a deflector member arranged to deflect the air flow from the pressure-reduction stage through the first noise-reduction member and thereby diffuse the air flow before it reaches the second noise-reduction member.

2. The regulator assembly of claim 1, wherein each noise reduction member comprises a mass of noise-reduction material positioned in the air flow path.

3. The regulator assembly of claim 1, wherein each noise-reduction member comprises a disc of sintered material.

4. The regulator assembly of claim 1, wherein the deflector member is positioned to divert air from a direct flow through the first noise-reduction member from the regulator device.

5. The regulator assembly of claim 1, wherein the pressure-reduction stage comprises a pressure-regulator, having an adjustable air flow.

6. The regulator assembly as claimed in claim 5, wherein which the pressure-regulator has a plurality of settings each of which is associated with a respective output air flow from the regulator, the adjustable air flow for each setting being substantially constant and independent of the pressure at which air is supplied from the said source over at least a pre-selected range of pressures.

7. The regulator assembly of claim 1, further including an odor filter located in the air flow path within the housing.

8. The regulator assembly of claim 1, further including a warning device exposed to the pressure at the air inlet port and operable to emit warning signal when the pressure at the air inlet port falls below a predetermined value.

9. A respirator system that comprises a regulator assembly of claim 1, wherein the air outlet port of the assembly is connected to a respirator head piece.

* * * * *

UNITED STATES PATENT AND TRADEMARK OFFICE

CERTIFICATE OF CORRECTION

PATENT NO. : 6,619,286 B2
DATED : September 16, 2003
INVENTOR(S) : Patel, Kaushik I.

It is certified that error appears in the above-identified patent and that said Letters Patent is hereby corrected as shown below:

Title Page,
Item [56], References Cited, U.S. PATENT DOCUMENTS, insert the following:

| | | |
|---|---|---|
| -- 5,720,280 | 2/1998 | Elstran et al. |
| 5,586,569 | 12/1996 | Hanning et al. |
| 5,526,805 | 6/1996 | Lutz et al. |
| 4,765,326 | 8/1988 | Pieper |
| 4,280,491 | 7/1981 | Berg et al. |
| 3,963,021 | 6/1976 | Bancroft |
| 3,926,208 | 12/1975 | Hoffman et al. |
| 3,811,400 | 5/1974 | Smilg -- |

FOREIGN PATENT DOCUMENTS, insert the following:

| | | |
|---|---|---|
| -- GB | 2302030A | 1/1997 |
| GB | 2130893 | 6/1984 |
| GB | 2032284 | 5/1980 |
| GB | 2026306A | 2/1980 |
| EP | 0921066 | 6/1999 |
| EP | 0586078 | 4/1998 |
| EP | 0631795 | 12/1997 |
| EP | 0766979 | 4/1997 |
| EP | 0602847 | 6/1994 |
| EP | 0349191 | 10/1993 |
| EP | 0303583 | 9/1991 |
| DE | 3032371 | 3/1982 |
| WO | WO 99/13945 | 3/1999 |
| WO | WO 97/46281 | 12/1997 |
| WO | WO 97/30753 | 8/1997 |
| WO | WO 97/13185 | 4/1997 -- |

UNITED STATES PATENT AND TRADEMARK OFFICE

CERTIFICATE OF CORRECTION

PATENT NO. : 6,619,286 B2
DATED : September 16, 2003
INVENTOR(S) : Patel, Kaushik I.

It is certified that error appears in the above-identified patent and that said Letters Patent is hereby corrected as shown below:

Column 6,
Line 9, “900” should read as -- 90º --.
Line 51, “spat” should read as -- seat --.

Signed and Sealed this

Tenth Day of February, 2004

JON W. DUDAS
*Acting Director of the United States Patent and Trademark Office*